(12) United States Patent
Wang et al.

(10) Patent No.: US 12,239,376 B2
(45) Date of Patent: Mar. 4, 2025

(54) HANDHELD OPTICAL IMAGING DEVICES AND METHODS

(71) Applicant: University of Washington, Seattle, WA (US)

(72) Inventors: Ruikang K. Wang, Seattle, WA (US); Shaozhen Song, Seattle, WA (US)

(73) Assignee: The University of Washington, Seattle, WA (US)

( * ) Notice: Subject to any disclaimer, the term of this patent is extended or adjusted under 35 U.S.C. 154(b) by 674 days.

(21) Appl. No.: 17/593,999

(22) PCT Filed: Mar. 27, 2020

(86) PCT No.: PCT/US2020/025152
§ 371 (c)(1),
(2) Date: Sep. 29, 2021

(87) PCT Pub. No.: WO2020/198562
PCT Pub. Date: Oct. 1, 2020

(65) Prior Publication Data
US 2022/0183553 A1 Jun. 16, 2022

Related U.S. Application Data

(60) Provisional application No. 62/824,863, filed on Mar. 27, 2019.

(51) Int. Cl.
*A61B 3/10* (2006.01)
*A61B 3/00* (2006.01)
(Continued)

(52) U.S. Cl.
CPC .............. *A61B 3/102* (2013.01); *A61B 3/005* (2013.01); *A61B 3/1208* (2013.01); *G01B 9/02091* (2013.01)

(58) Field of Classification Search
CPC ..... A61B 3/005; A61B 3/0058; A61B 3/0066; A61B 3/102; A61B 3/1208; A61B 3/1225;
(Continued)

(56) References Cited

U.S. PATENT DOCUMENTS 8,594,757 B2    11/2013   Boppart
9,013,555 B2     4/2015   Wang
(Continued)

FOREIGN PATENT DOCUMENTS

CN       202699100 U       1/2013
WO     2012166116 A1      12/2012
(Continued)

OTHER PUBLICATIONS

International Search Report and Written Opinion for PCT/US2020/025152, mailed Jun. 12, 2020, 8 pages.
(Continued)

*Primary Examiner* — Jack Dinh
(74) *Attorney, Agent, or Firm* — Christensen O'Connor Johnson Kindness PLLC

(57) ABSTRACT

Handheld optical imaging devices and methods are disclosed herein. In an embodiment, an optical coherence tomography (OCT) system includes an OCT probe that is configured as a hand-held probe for imaging an eye of a patient, the OCT probe includes: an OCT optical system configured to direct a source OCT signal to the eye and configured to capture OCT scan signal returning from the eye; and an on-probe display carried by a handle, wherein the on-probe display is configured to display imaging data of the eye of a patient to an operator during OCT imaging.

15 Claims, 14 Drawing Sheets

(51) Int. Cl.
*A61B 3/12* (2006.01)
*G01B 9/02091* (2022.01)

(58) Field of Classification Search
CPC .............. A61B 5/1128; A61B 2503/04; G01B 9/02091
See application file for complete search history.

(56) References Cited

U.S. PATENT DOCUMENTS

| | | |
|---|---|---|
| 2009/0040306 A1 | 2/2009 | Foote et al. |
| 2009/0268020 A1 | 10/2009 | Buckland et al. |
| 2012/0140238 A1 | 6/2012 | Horn |
| 2016/0228000 A1 | 8/2016 | Spaide |
| 2017/0032564 A1 | 2/2017 | Dastmalchi et al. |

FOREIGN PATENT DOCUMENTS

| | | |
|---|---|---|
| WO | 2014051274 A2 | 4/2014 |
| WO | 2014051274 A3 | 4/2015 |
| WO | 2016205760 A1 | 12/2016 |
| WO | 2018119009 A1 | 6/2018 |
| WO | 2019147871 A1 | 8/2019 |

OTHER PUBLICATIONS

Adams, G. G. W., et al. "Retinal haemorrhages in an infant following RetCam screening for retinopathy of prematurity." Eye 18.6 (2004): 652-653.
Jung, Woonggyu, et al. "Handheld optical coherence tomography scanner for primary care diagnostics." IEEE Transactions on Biomedical Engineering 58.3 (2011): 1-9.
Campbell, J. Peter, et al. "Handheld optical coherence tomography angiography and ultra-wide-field optical coherence tomography in retinopathy of prematurity." JAMA ophthalmology 135.9 (2017): 977-981.
Carr, Ronald E., "Physiology of the Human Eye and Visual System," American Journal of Ophthalmology, 89.2 (1980): 314.
Early Treatment for Retinopathy of Prematurity Cooperative Group. "The incidence and course of retinopathy of prematurity: findings from the early treatment for retinopathy of prematurity study." Pediatrics 116.1 (2005): 15-23.
Geiger, Andreas, et al. "Automatic camera and range sensor calibration using a single shot." 2012 IEEE international conference on robotics and automation. IEEE, 2012.
Gilbert, Clare, et al. "Characteristics of infants with severe retinopathy of prematurity in countries with low, moderate, and high levels of development: implications for screening programs." Pediatrics 115.5 (2005): e518-e525.
Gilbert, Clare. "Retinopathy of prematurity: a global perspective of the epidemics, population of babies at risk and Implications for control." Early human development 84.2 (2008): 77-82.
International Committee for the Classification of Retinopathy of Prematurity. "The international classification of retinopathy of prematurity revisited." (Reprinted) Archives of ophthalmology (Chicago, Ill.: 1960) 123.7 (2005): 991-999.
Hartnett, Claire, Michael O'Keefe, and Georgi Graschew. "Screening for retinopathy of prematurity." Telemedicine Techniques and Applications. IntechOpen, 2011.
Hernandez-Vargas, Jose A., et al. "Comparison Of Optical Coherence Tomography Macular Findings In 5 Year-old Patients With A History Of Pre-threshold Or Threshold Retinopathy Of Prematurity Treated With Intravitreal Bevacizumab As Monotherapy." Investigative Ophthalmology & Visual Science 53.14 (2012): 4683-4683.
Huang, David, et al. "Optical coherence tomography." science 254.5035 (1991): 1-12.
Iannaccone, Alessandro . "Optical coherence tomography in rare pediatric cases." Retina Today (2012): 66-69.
Ju, Myeong Jin, et al. "Effective bidirectional scanning pattern for optical coherence tomography angiography." Biomedical optics express 9.5 (2018): 2336-2350.
Kirby, Mitchell A., et al. "Why choroid vessels appear dark in clinical OCT images." Proc. SPIE 10474, Ophthalmic Technologies XXVIII, 1047428 (2018).
Lad, Eleonora M., et al. "Incidence of retinopathy of prematurity in the United States: 1997 through 2005." American journal of ophthalmology 148.3 (2009): 451-458.
Lorenz, Birgit, et al. "Wide-field digital imaging based telemedicine for screening for acute retinopathy of prematurity (ROP). Six-year results of a multicentre field study." Graefe's Archive for Clinical and Experimental Ophthalmology 247.9 (2009): 1251-1262.
Maldonado, Ramiro S., and Cynthia A. Toth. "Optical coherence tomography in retinopathy of prematurity: looking beyond the vessels." Clinics in perinatology 40.2 (2013): 1-39.
Maldonado, Ramiro S., et al. "Optimizing hand-held spectral domain optical coherence tomography imaging for heonates, infants, and children." Investigative ophthalmology & visual science 51.5 (2010): 2678-2685.
Moore, Anthony T. "Handheld OCT Comes of Age." Investigative ophthalmology & visual science 56.8 (2015): 4546-4546.
Muni, Rajeev H., et al. "Retinoschisis detected with handheld spectral-domain optical coherence tomography in neonates with advanced retinopathy of prematurity." Archives of Ophthalmology 128.1 (2010): 57-62.
National Eye Institute, "Retinopathy of Prematurity," <https://www.nei.nih.gov/learn-about-eye-health/eye-conditions-and-diseases/retinopathy-prematurity> [Accessed on Jul. 8, 2019], 6 pages.
Ng, Eugene YJ, and Bernadette Lanigan. "Fundus fluorescein angiography in the screening for and management of retinopathy of prematurity." Journal of Pediatric Ophthalmology & Strabismus 43.2 (2006): 85-90.
Puliafito, Carmen A., et al. "Imaging of macular diseases with optical coherence tomography." Ophthalmology 102.2 (1995): 217-229.
Song, Shaozhen, et al. "Development of a clinical prototype of a miniature hand-held optical coherence tomography probe for prematurity and pediatric ophthalmic imaging." Biomedical Optics Express 10.5 (2019): 2383-2398.
Song, Shaozhen, et al. "Robust numerical phase stabilization for long-range swept-source optical coherence tomography." Journal of biophotonics 10.11 (2017): 1-25.
Viehland, Christian, et al. "Ergonomic handheld OCT angiography probe optimized for pediatric and supine imaging." Biomedical Optics Express 10.5 (2019): 2623-2638.
Vinekar, Anand, et al. "Understanding clinically undetected macular changes in early retinopathy of prematurity on spectral domain optical coherence tomography." Investigative ophthalmology & visual science 52.8 (2011): 5183-5188.
Wojtkowski, Maciej, et al. "Ultrahigh-resolution, high-speed, Fourier domain optical coherence tomography and methods for dispersion compensation." Optics express 12.11 (2004): 2404-2422.
Wu, Carolyn, Robert A. Petersen, and Deborah K. VanderVeen. "RetCam imaging for retinopathy of prematurity screening." Journal of American Association for Pediatric Ophthalmology and Strabismus 10.2 (2006): 107-111.
Yang, Jianlong, et al. "Handheld optical coherence tomography angiography." Biomedical optics express 8.4 (2017): 2287-2300.
Yen, Kimberly G., et al. "Telephotoscreening to detect retinopathy of prematurity: preliminary study of the optimum time to employ digital fundus camera imaging to detect ROP." Journal of American Association for Pediatric Ophthalmology and Strabismus 6.2 (2002): 64-70.
Yin, Xin, Jennifer R. Chao, and Ruikang K. Wang. "User-guided segmentation for volumetric retinal optical coherence tomography images." Journal of biomedical optics 19.8 (2014): 086020.
Yokoi, Tadashi, et al. "Vascular abnormalities in aggressive posterior retinopathy of prematurity detected by fluorescein angiography." Ophthalmology 116.7 (2009): 1377-1382.

(56) References Cited

OTHER PUBLICATIONS

Yousefi, Siavash, Zhongwei Zhi, and Ruikang K. Wang. "Eigendecomposition-based clutter filtering technique for optical microangiography." IEEE transactions on biomedical engineering 58.8 (2011): 1-18.

Zhang, Qinqin, Jingang Wang, and Ruikang K. Wang. "Highly efficient eigen decomposition based statistical optical microangiography." Quantitative imaging in medicine and surgery 6.5 (2016): 557-563.

International Preliminary Report on Patentability mailed Sep. 28, 2021, issued in corresponding International Application No. PCT/US2020/025152, filed Mar. 27, 2020, 6 pages.

Viehland, Christian, "Imaging of pediatric pathology in the intensive care nursery using a custom handheld, ultra-compact, swept-source OCT probe (Conference Presentation)" Transcript, 2018.

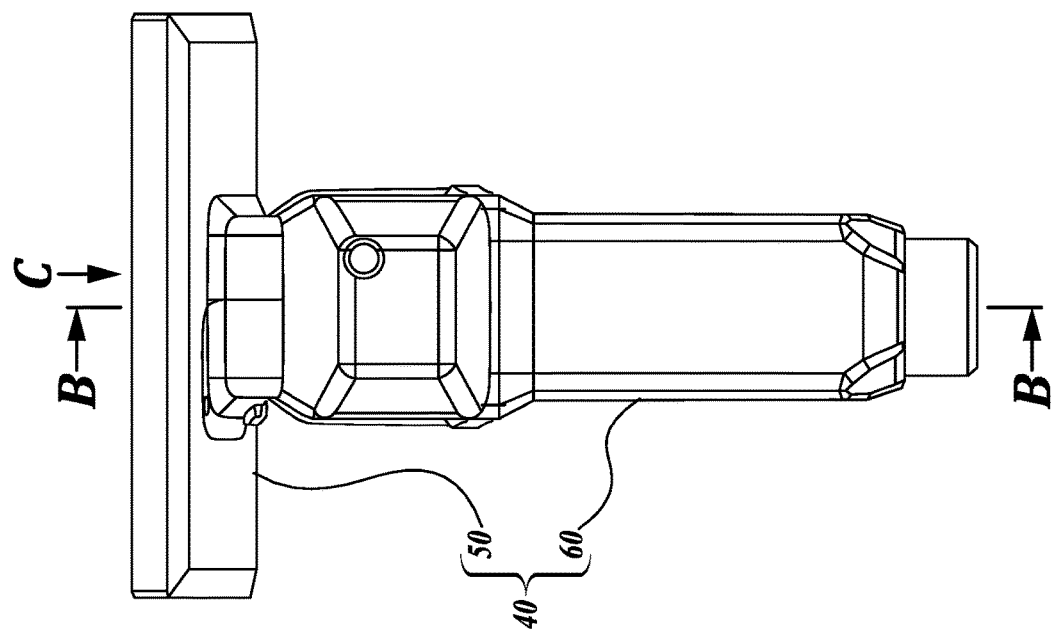
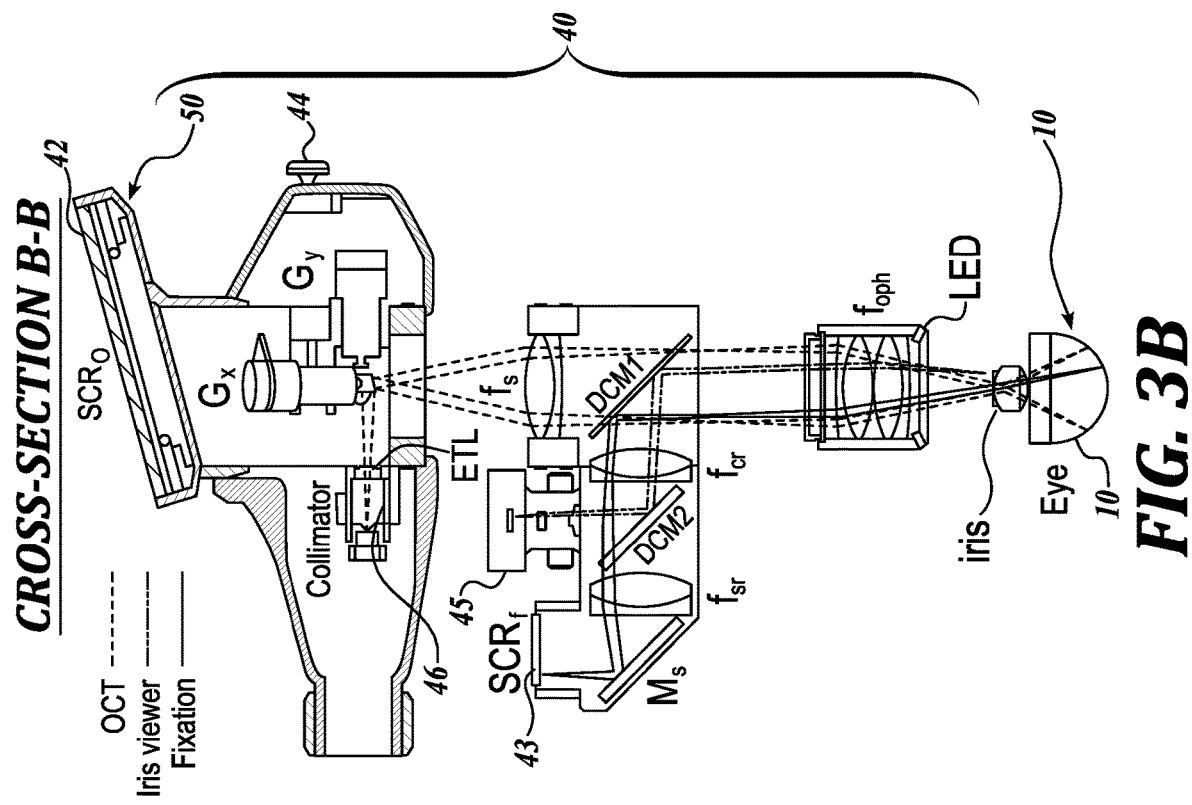
*FIG. 3A*
*FIG. 3B*

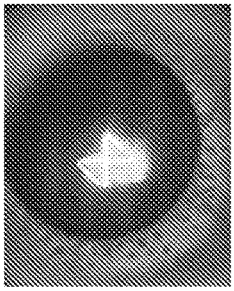
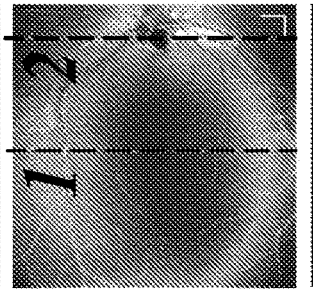
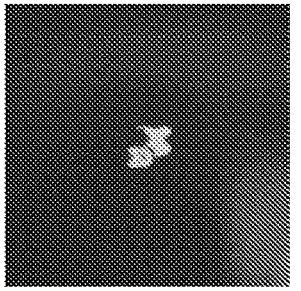
FIG. 6C
FIG. 6D
FIG. 6E
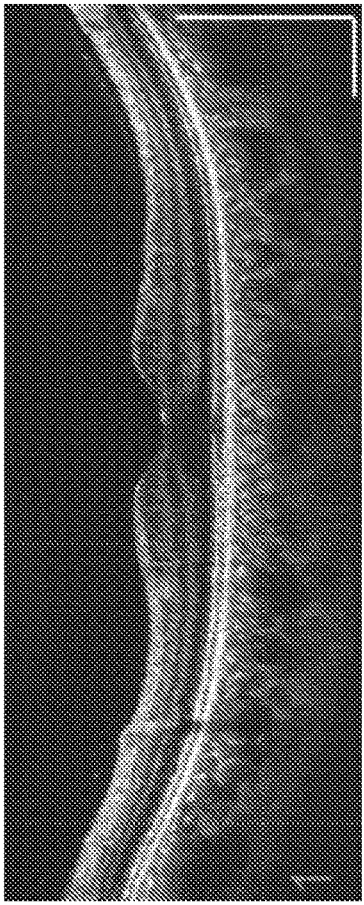
FIG. 6A
FIG. 6B

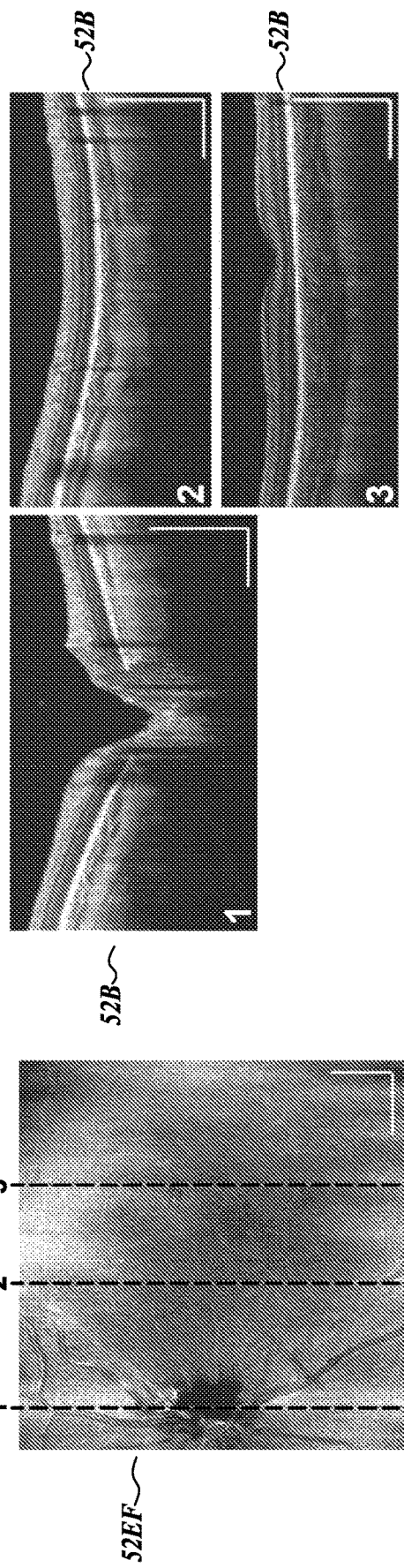
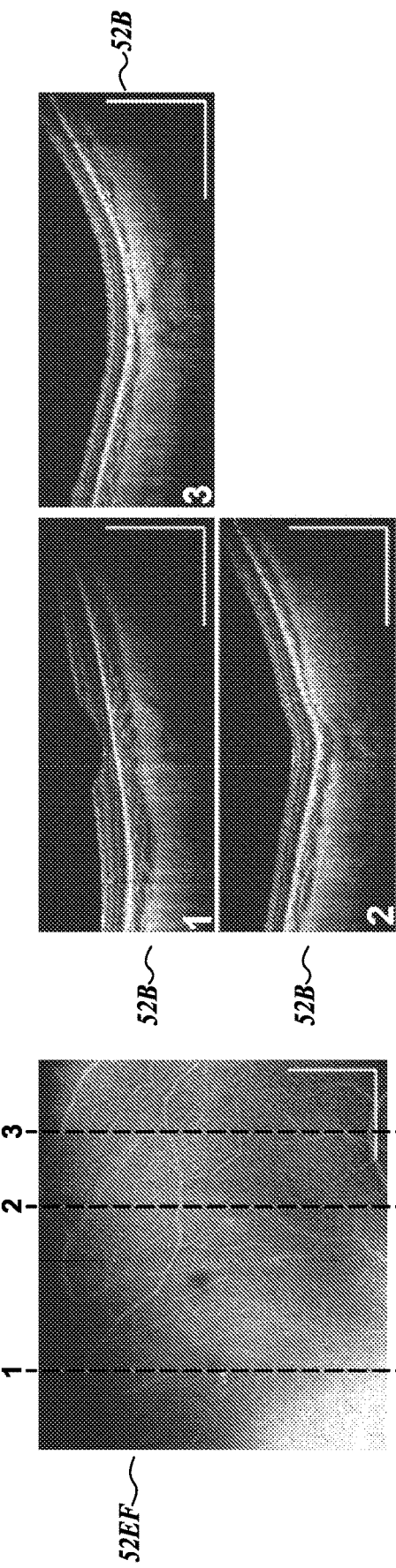
FIG. 9A  FIG. 9B  FIG. 9C  FIG. 9D

HANDHELD OPTICAL IMAGING DEVICES AND METHODS

CROSS-REFERENCE TO RELATED APPLICATIONS

This application claims the benefit of U.S. Provisional Application No. 62/824,863 filed on Mar. 27, 2019, the contents of which are incorporated herein by reference in their entirety.

BACKGROUND

Childhood blindness refers to a group of diseases and conditions, which, if not treated in time, can lead to a permanent vision loss that can severely impact quality of life of patients and their family. It has been reported that retinopathy of prematurity (ROP), a vision-threatening disease associated with abnormal retinal vascular development, is a prevalent disease in premature infants and a leading cause of blindness in children in the developed as well as developing countries. It is estimated that over 50, 000 children are blind from ROP worldwide. The basic reason for high incidence of ROP nowadays is that a prevalence of infants being born premature (less than 1500 g) has increased tremendously. Most ROP regress spontaneously without treatment by the process of involution or evolution from a vasoproliferative phase to a fibrotic phase; however, more severe cases need therapeutic treatment to prevent blindness. This calls for an effective neonatal screening and follow-up exams to assist early diagnosis and decision making Binocular Indirect Ophthalmoscope (BIO) is recognized as the gold standard for screening and diagnosis of ROP. The advantage of BIO is its capability of complete documentation of ROP. However, there is also a number of disadvantages in BIO, including: 1) being time-consuming; 2) being painful and uncomfortable for the infants due to the use of speculum and indenter; and 3) having poor interobserver agreement.

Efforts continue in developing and clinically testing ophthalmic imaging instruments for ROP screening. With the advent of hand-held digital fundus imaging device, e.g. RetCam (Massie Laboratories, Inc., Pleasanton, CA, USA), the screening of ROP using this digital imaging device has proved a potential alternative to BIO. With this conventional technology, a contact lens is placed on the cornea during the retinal screening. Compared to the BIO, the digital fundus camera is easier to use, and can provide high-resolution fundus image with acceptable reproducibility. However, in neonatal situations the image quality is sometimes poor and limits the diagnosis of ROP. This limitation may be attributable to: 1) the difficulty in imaging the small eyes of infants with small palpebral fissures, which prevent good corneal contact with the lens nosepiece; 2) insufficient sensitivity; and 3) poor mydriasis. Other limitations for neonatal ROP screening using the digital fundus camera includes painful and uncomfortable screening procedure, and sometimes retinal hemorrhages after screening.

With other conventional technologies, Fluorescein Angiography (FA) is often used as a diagnostic tool for ROP in infants at risk. However, the limitation of FA is the requirement of dye injection, which raises severe medical safety concerns especially for premature infants. Additionally, significant time and cost are added to the procedure.

Optical coherence tomography (OCT) is a known noncontact and noninvasive imaging technique for detailed assessment of microanatomy and pathology of the retina. Furthermore, optical coherence tomography angiography (OCTA) has the capability of detecting intrinsic motion within different layers of the retina to depict blood flow. Therefore, OCTA can provide similar blood vessel network information to that of FA, but without fluorescein dye injection. However, commercial OCT systems are tabletop units for adults and patients who are cooperative and are able to maintain a stable position in a chin rest during the test, thus not amendable to imaging infants.

Some commercially available portable OCT systems for neonatal ROP screening are Leica Envisu™ C-class (Leica Microsystems Inc., IL, USA, Formerly Bioptigen Envisu™) and Optovue iStand™ (Optovue Inc., Fremont, CA, USA). Envisu™ is a portable spectral domain (SD)-OCT system with hand-held probe. The OCT engine (32 kHz A-line rate) of this system is mounted into a medical cart, making it possible to adapt different scenarios in a medical center. The hand-held probe of the system features lightweight design with refraction correction from +10 to −12 D. Optovue iStand™ is also a SD-OCT based potable retinal imaging system (26 kHz A-line rate) with a scanner head mounted on an armature for imaging patients in supine position. Besides, Optovue has a fundus camera that can guide OCT to the region of interest for imaging A number of research groups across several countries have reported their neonatal retinal imaging results using these systems. However, the relatively low A-line rate of both systems limit their ability to perform OCTA scans in hand-held configuration. Thus, these available commercial systems have limitation in accurate diagnosis ROP at early stage both in terms of system operability and image quality.

Other conventional technologies have attempted the development of high-performance hand-held OCT/OCTA system using high-speed (over 100 kHz) swept-source laser for ROP screening. Some reported their light weight, 100 kHz A-line-rate handheld probe for OCTA applications and demonstrated high-quality OCTA images in awake adults and anesthetized infants. Some reported a 200 kHz A-line-rate handheld OCTA probe designed on an innovative '5F' (focus) optical system, demonstrating OCTA image of foveal area and optical nerve head.

However, the conventional systems do not address difficulties in obtaining eye images from all patients, and especially from infants. Accordingly, systems and methods are needed for improved imaging of eyes, especially with infants.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

[Restatement of Claims Here after the Final Form of Claims is Agreed Upon.]

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 3A shows a front view of a hand-held OCT probe in accordance with an embodiment of the present technology;

FIG. 3B shows a simplified section view B of the system shown in FIG. 2A;

FIGS. 6A-6E show images displayed on an on-probe display in accordance with an embodiment of the present technology;

FIGS. 9A-9D show sample OCT structural imaging results acquired from pre-mature infants by a hand-held unit in accordance with an embodiment of the present technology.

DETAILED DESCRIPTION

Briefly, the embodiments of the inventive technology are directed to systems and methods for imaging eye or other body parts (e.g., skin, ear, nose, etc.). The inventive technology may be particularly well suited for imaging eyes of infants and young children. In some embodiments, the inventive systems include an integrated handheld OCT probe, having with high-speed, wide-field angiography.

In some embodiments, a portable OCT system is based on a 200 kHz swept-source laser. The inventive systems and methods may include a direct-view iris camera, on-probe display for operator when performing imaging, and on-probe controls of motorized optomechanical components for improved imaging efficiency and usability in a clinical environment. These different images can be displayed in real time on the on-probe display that is attached to a handle of the hand-held OCT probe. In operation, the operator (e.g., an ophthalmologist) relies on these images to improve aiming of the hand-held OCT probe toward the patient's eye or other body part. In different embodiments, the hand-held ophthalmic OCT system incorporates a high-throughput OCT engine, a highly integrated custom designed probe, multiple stages of data processing and data visualizations to deliver OCT and OCTA images.

OCT probe positioning procedure generally requires that the operator must control six degrees of freedom (DoF) simultaneously, including all three translational DoF and three rotational DoF of the probe. The inventive hand-held OCT system addresses this requirement by providing multiple visual feedbacks for probe positioning. Based on improved control of the probe, the data acquisition speed is increased and the overall duration of the imaging process is reduced.

Figures 1A, 1B:
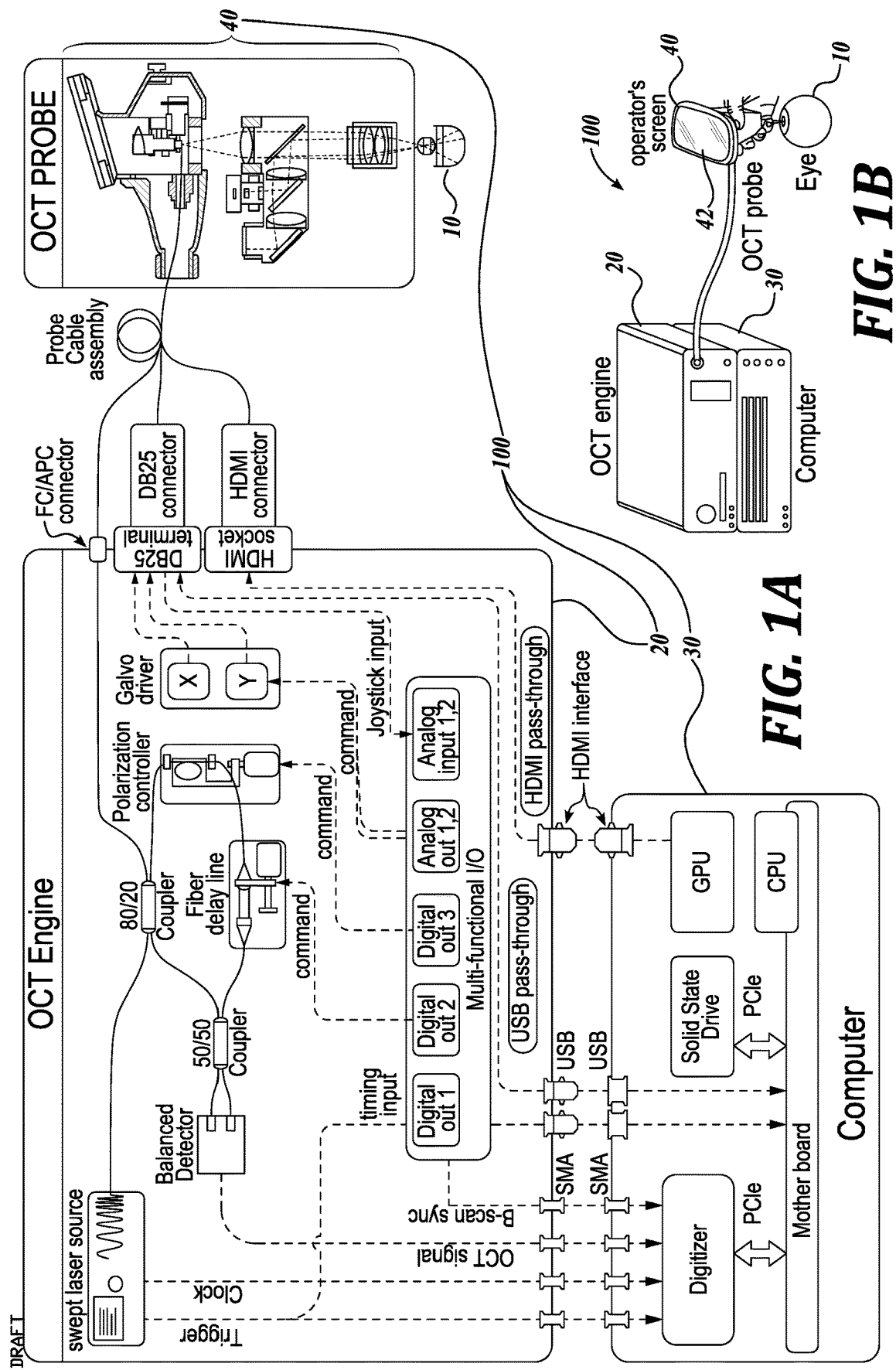
FIG. 1A shows a partially schematic view of a hand-held ophthalmic OCT system hardware in accordance with an embodiment of the present technology.
FIG. 1B shows an isometric view of the system shown in FIG. 1A.

FIG. 1A shows a partially schematic view of a hand-held ophthalmic OCT system hardware in accordance with an embodiment of the present technology. In some embodiments, the hand-held ophthalmic OCT system 100 includes an OCT imaging engine 20, a computer unit (also referred to as a computer) 30 and a hand-held probe 40. These components may be individually self-enclosed, with detachable connectors for interconnecting the units. Both the imaging engine 20 and computer module 30 may be assembled within a standard rack enclosure, for example a portable 19-inch enclosure occupying a rack space of 4U height, therefore resulting in the final system measures of 19×21.5× 14-inch space, which can be easily transported to clinical bed-side for imaging. Some components and subsystems of the OCT system 100 are described below.

Interferometer

In some embodiments, the OCT imaging engine 20 includes a 20:80 fiber coupler and a 50:50 fiber coupler. The first coupler provides a split of 20% laser energy delivered to the sample arm port on the front panel of the OCT imaging engine. The other arm of the first coupler may carry the remaining light to a motorized, variable optical delay line, where iris diaphragms adjust the reference power. The reference signal and the returned signal from the sample arm can be combined at the second coupler, and then split 50/50 onto the balanced photodetectors for signal detection, which is integrated within the laser module (also referred to as swept laser source or source of light). The OCT imaging engine 20 may include different numbers or arrangements of digital and analog outputs, different couplers for laser light, etc. The interconnects (i.e., USB, SMA, HDMI, etc.) among the components of the system are also just an example configuration. A person of ordinary skill would know that other configurations of the interconnects are also possible.

Electronic Peripherals

In some embodiments, the electronics of the OCT imaging engine includes: a multifunction 110 (e.g., a NI-USB 6341 from National Instruments); a canner servo-drivers: dual-axis galvo servo driver (e.g., Cambridge Technologies 673) that drives the scanners inside the hand-held probe; opto-mechanical controllers, including a motorized optical delay line, and a single-paddle, motorized polarization controller; and pass-through signals for OCT probe (the electronic signals required by the hand-held probe is passed through from the computer to the front panel of the OCT imaging engine). The sample NI-USB 6341 device can be used for multiple purposes: a) dual channel analog output for generating galvanometer scanning signals; b) dual channel analog input for monitoring user inputs from the joystick on hand-held probe; c) one channel digital waveform output for digitizer synchronization; and/or d) two channels of digital waveform output for controlling opto-mechanical components, including optical delay line and polarization controller. In some embodiments, the above-described setup simplifies the connection interface between the probe and the rest of the imaging system. The signal pass-through assembly may include an USB interface for iris viewer camera, an USB interface for fixation display, and an HDMI interface for on-probe display.

Computer

An example computer (also referred to as a computing unit) 30 is illustrated in FIG. 1A. However, in different embodiments the computer 30 may include different configurations (e.g., different drives, additional CPUs, multiple GPUs or no GPUs, additional controllers, etc.). In some embodiments, the computing unit 30 is equipped with a high-speed PCIe-based digitizer (e.g., ATS9373, Alazar Technologies, Inc.) for collecting OCT signal and real-time display. The raw data can also be streamed onto hard-drive for later processing. In order to minimize the latency for data streaming, PCIe-based solid state drive (e.g., MZ-V7E1T0BW, Samsung Electronics Co., Ltd.) provides a continuous disk writing speed that is capable of handling the data throughput from digitizer without significant delay during writing to hard-drive. In different embodiments, custom software is developed with C++ and LabVIEW platform, that provides a graphical user interface (GUI) and functionalities of real-time 2D preview imaging, as well as 3D data collection and playback.

OCT Probe

The OCT probe 40 directs optical signals (OCT probing beam) toward eye 10 of a patient (e.g., an infant), and receives the reflected optical signal that is captured and processed by the OCT system 100. A sample laser source of the OCT system 100 is described in conjunction with FIGS. 2A-2D below.

FIG. 1B shows an isometric view of the system shown in FIG. 1A. In operation, the operator holds the OCT probe 40 by the handle, while observing eye images on a display (screen) 42. Therefore, the operator does not need to divide her attention between the OCT probe and a remotely positioned monitor, as is the case with the conventional systems. Furthermore, changing a position and/or direction of the OCT probe 40 changes the images on the display 42, therefore providing an almost real-time feedback to the operator who observes the images on the display 42.

Laser Source

FIGS. 2A-2D show swept laser source characteristics, each graph displaying one cycle of laser sweep, during 5-microsecond period in accordance with an embodiment of the present technology. The horizontal axis in each figure shows time in microseconds. The vertical axes in the graphs show: a trigger signal in FIG. 3A, an optical power output in FIG. 3B; a Mach Zehnder interferometer (MZI) clock signal in FIG. 3C; and an instantaneous clock frequency in FIG. 3D.

Figure 2C:
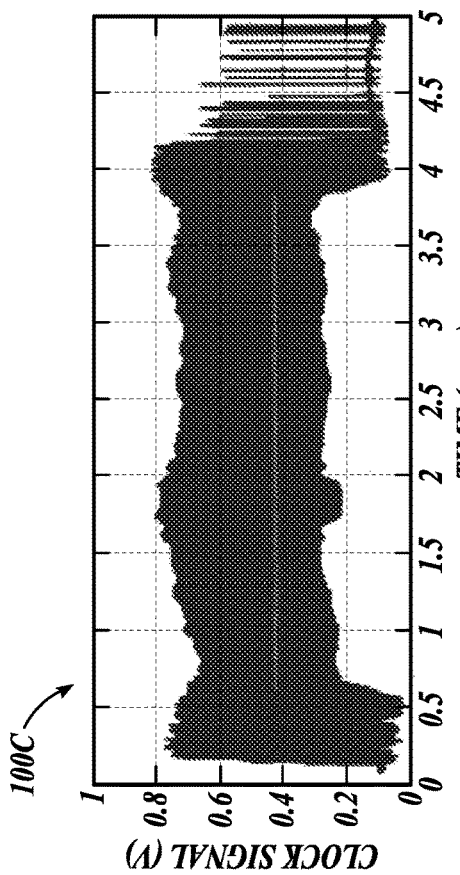
FIGS. 2A-2D show swept laser source characteristics, each graph displaying one cycle of laser sweep, during 5-microsecond period in accordance with an embodiment of the present technology.
Figure 2D:
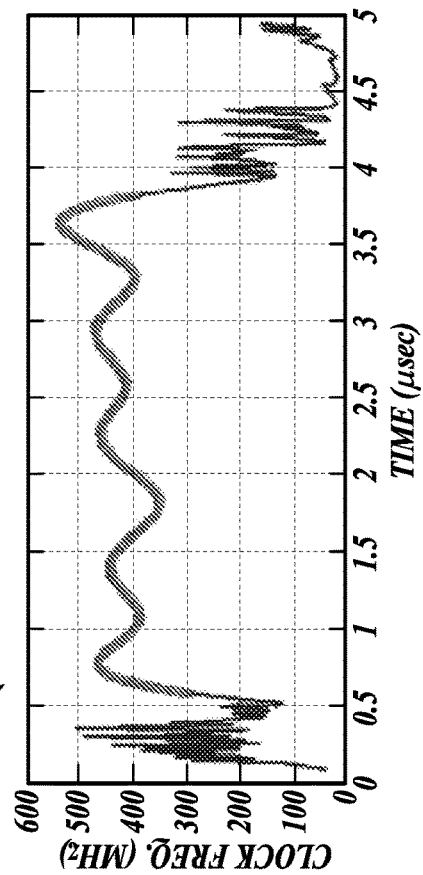

In some embodiments, a 200-kHz MEMS-tunable swept laser source (e.g., AXP50124-3 of AXSUN Technologies Inc.) can be used as the light source that provides a central wavelength of 1051 nm and a spectral tuning range of 105.2 nm. The sample laser has an averaged output power of 24.4 mW (FIG. 2B). In some embodiments, only one direction of the sweep is utilized, with valid sweeping time of 3.24 µs out of 5.0 µs sweep period, giving a sweep duty cycle of 82.9%. A Mach Zehnder interferometer (MZI) may be integrated inside the laser source module to provide a sampling clock for the data acquisition digitizer, thus providing a linear-K sampling of the spectrum, as shown in FIG. 2C. During the invalid sweep time (>3.24 µs post-trigger), the MZI clock signal is invalid. The digitizer may be programmed to switch to a dummy clock at invalid sweep times to prevent malfunctions of ADC (analog to digital converter) on the digitizer. In the illustrated embodiments, the average sampling clock is 428.5 MHz, providing 1376 clocks per sweep.

FIG. 3A shows a front view of a hand-held OCT probe in accordance with an embodiment of the present technology. The hand-held OCT probe 40 includes a handle 60 and an on-probe display 50. In operation, the operator holds the handle 60 while observing the images on the on-probe display 50.

Figure 2A:
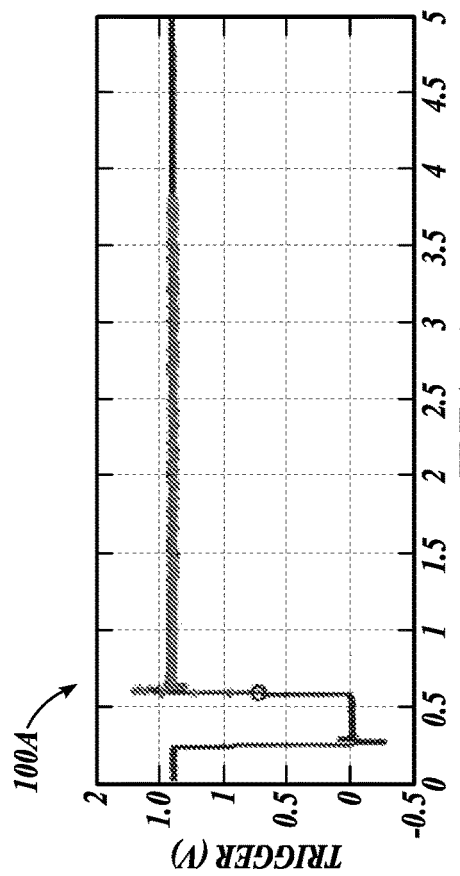
Figure 2B:
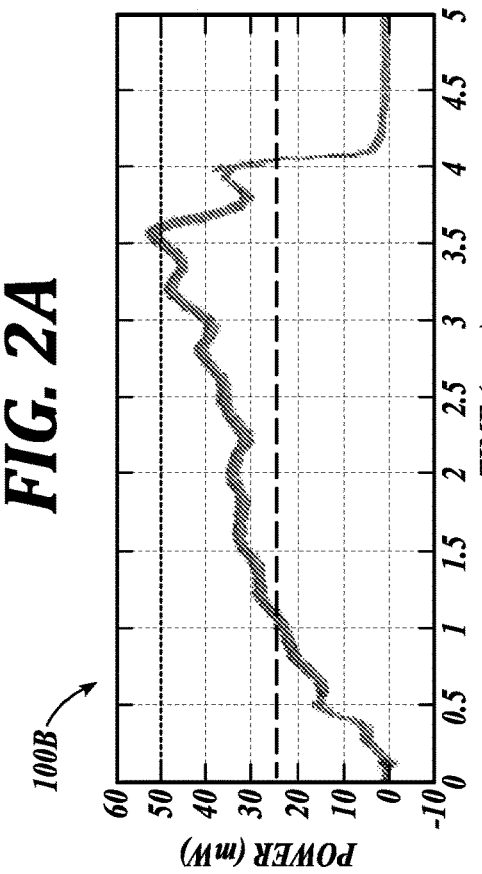

FIG. 3B shows a simplified section view B of the system shown in FIG. 2A. The view of FIG. 3B is partially exploded and internal connections including optical fiber and electrical wires are omitted. Furthermore, outer housing and mechanical positioning components are simplified for easier understanding. In some embodiments, the hand-held OCT probe 40 includes: SCRo—Screen for operator and SCRf—Screen for subject eye fixation 43, the image also being visible to the subject. The probe 40 also includes Gx/Gy—Galvanometers, fs—Scanning lens, DCM1—Dichroic mirror to separate OCT beam, DCM2—Dichroic mirror to separate iris viewer light, Ms—Reflection mirror for fixation screen, fsr—Fixation screen relay lens, fcr—iris viewer CCD relay lens, and foph—Ophthalmic lens.

In some embodiments, the OCT probe 40 includes a fast response electrically tunable lens (ETL), which is an active optical component that can change refractive power when driven by electric signal. Such ETL lens is commercially available, for example, as model EL-10-30 from Optotune, Switzerland. With the ETL lens, the operator can quickly adjust the focus to adapt to different conditions of newborn eyes. Such rapid adjustment of focus using ETL lens during OCT/OCTA imaging may be beneficial in the imaging and quantification of the vitreous opacities and suspension particles in the vitreous chamber, which facilitates clinical diagnosis for a number of eye conditions in the preemies and newborn infants.

Figure 3C:
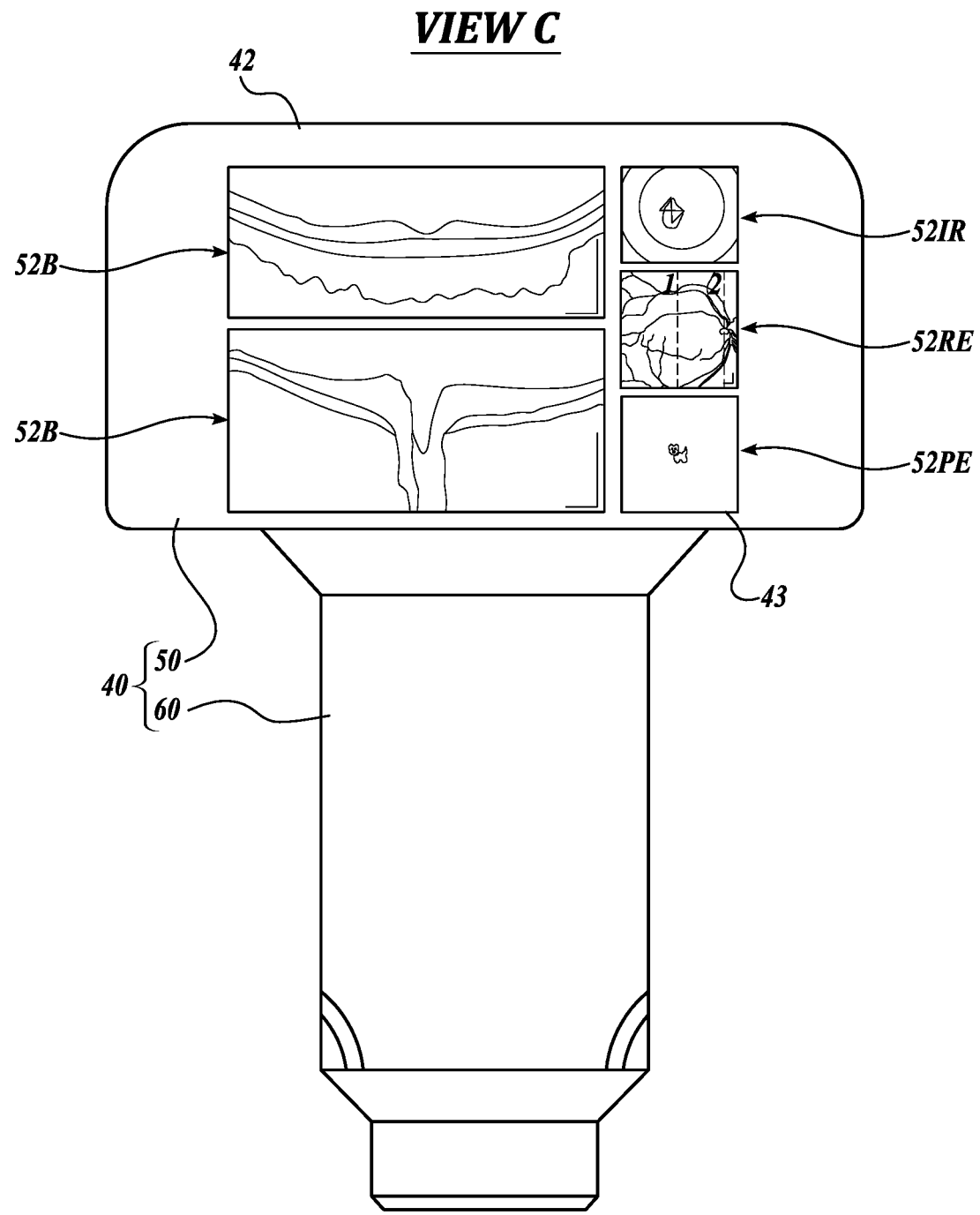
FIG. 3C shows a simplified back view C of the system shown in FIG. 2A.

FIG. 3C shows a simplified back view C of the system shown in FIG. 2A. FIG. 3C illustrates sample images displayed on the screen 42 of the display 50. Some details of the embodiments shown in FIGS. 3A-3C are discussed below.

OCT Optics

In some embodiments, the OCT laser beam (dash line) enters the hand-held probe from a fixed focus fiber collimator 46 with an initial 1/e2 beam diameter of 3.4 mm. The beam is scanned by a paired X-Y galvo scanning mirror set (e.g., 6200H/XY, Cambridge Technology, shown as Gx/Gy), forming raster sampling patterns that consist of a series of fast (x-axis) and slow (y-axis) scans. The driving signals that generate the scan pattern are provided by the OCT software, and then delivered to the servo-drivers as analogue waveform of maximum amplitude of +/−10V. Galvo scanners are configured to +/−20° mechanical deflection angle at +/−10V input. In the illustrated embodiment, scanning beam first enters an achromatic lens (fs in f=50 mm), and then after 75 mm distance, enters a paired achromatic lens group, functioning as ophthalmic lens (effective f=25 mm, foph in FIG. 3B). This set of combined lenses works as a 2× telescope, which amplifies the scanning angle from about +/−20° to about +/−36° such that the field-of-view on retina is extended. The beam diameter is also de-magnified to 1.7 mm at iris plane.

Iris Viewer

Iris viewer is integrated into the hand-held probe in order to assist the operator for rapid positioning and alignment of the OCT probe with the optical axis of subject eye. In the illustrated embodiment, the working wavelength for the iris viewer (phantom line) is 805 nm, as the subject iris is illuminated by a ring of 850 nm LEDs underneath the ophthalmic lens casing. The benefit of such near-IR illumination is that the iris viewer maintains excellent functionality at low light environment, which eliminates the requirements for pupil dilation. Back-scattered light from subject's iris goes through the ophthalmic lens, is reflected by two dichroic mirrors, and then received by a ⅓-inch format, monochrome CMOS camera 45 (e.g., MT9M021 from The Imaging Source LLC.). The camera 45 (also referred to as a detector) sends real-time video to the PC, which is displayed on the operator's screen (SCRo) for visual feedback of probe positioning. The two dichroic mirrors are: DCM1, a long-pass dichroic mirror (e.g. DMLP900R, Thorlabs Inc.) with a cut-off wavelength at 900 nm, inserted between the scanning lens (fs) and the ophthalmic lens (foph); and DCM2, a short-pass dichroic mirror (e.g. DMSP805, Thorlabs Inc.), cut-off wavelength at 805 nm to separate the iris viewer optical path and fixation screen optical path. The size of DCM1 may be 36×25×1 mm (L×W×H), placed at 45° to OCT beam axis, providing 25×25 mm aperture for the scanning optics without sacrificing OCT scan range. OCT imaging was tested with and without installing DCM1 mirror, and the image quality degradation due to installation of DCM1 was negligible. A simplified image from the iris viewer is presented in FIG. 3C as 52IR.

Fixation Screen

The purpose of the fixation screen is to provide a fixation target for the test subject to stare at during OCT imaging operations. In some embodiments, a 0.96-inch, 128×128 pixel OLED display module is used to display simple graphics. Light emitted from the OLED screen passes through lenses fsr, fcr, dichroic mirror DCM2, is reflected by DCM1, and then delivered to subject's eye through ophthalmic lens foph. In different embodiments, different patterns generated by the computer can be displayed. However, for adults who are typically cooperative during imaging, a plus marker "+" is displayed for maintaining fixation. For pediatric imaging, simple animations can be played on the screen to attract attention from young children. This animation display is particularly useful to promote their cooperation so that they can maintain still during the OCT/OCTA scans. However, in some embodiments the fixation screen is disabled for infant imaging due to their incapability to follow instructions and looking at the fixation screen. An example of the fixation screen contents are shown as a simplified image 52PE in FIG. 3C.

On-Probe Display

For convenience and guidance of the OCT imaging system operator, a high-definition screen 42 (SCRo) is fitted onto the hand-held probe, so that the OCT imaging software GUI (graphical user interface) is displayed right on the probe (e.g., images 52xx in FIG. 3C). The screen may be a 5.9-inch LCD screen at 1920×1080-pixel resolution. Screen may be powered through USB bus, while the video signal is mirrored from the computer display, which is delivered by HDMI interface. In some embodiments, the screen assembly weighs only 146 grams, adding a negligible weight burden for the operator holding the probe. Since the screen 42 is mounted on the probe 40, the operator does not need to look away from the subject while positioning the probe and optimizing image quality, which is an important feature that improves the safety of subject and the efficiency for data collection in pediatric imaging applications.

In some embodiments, the screen 42 displays OCT images 52B (e.g., two mutually orthogonal B-scans), iris viewer image 52IR, retina viewer image 52RE, and fixation image 52PE (e.g., a cross or an image for pediatric imaging).

Operating Switch Controls

An operating switch 44 (e.g., an analog joystick control) serves as an on-probe input for the convenience of operator. The illustrated operating switch has dual-axis potentiometer and a push button. In some embodiments, the operating switch is configured to provide bi-directional input command for adjusting reference optical delay when the joystick is steered up/down; and adjusting polarization when steered left/right. Push button may serve as "start acquisition" trigger. The sample joystick is wired through probe cable, which is fed to the multifunctional I/O device for communication with control software. In different embodiments, operators engage a separate foot pad, thus using foot motion to control the reference optical delay in order to position the OCT image within the system ranging distance.

Figure 4:
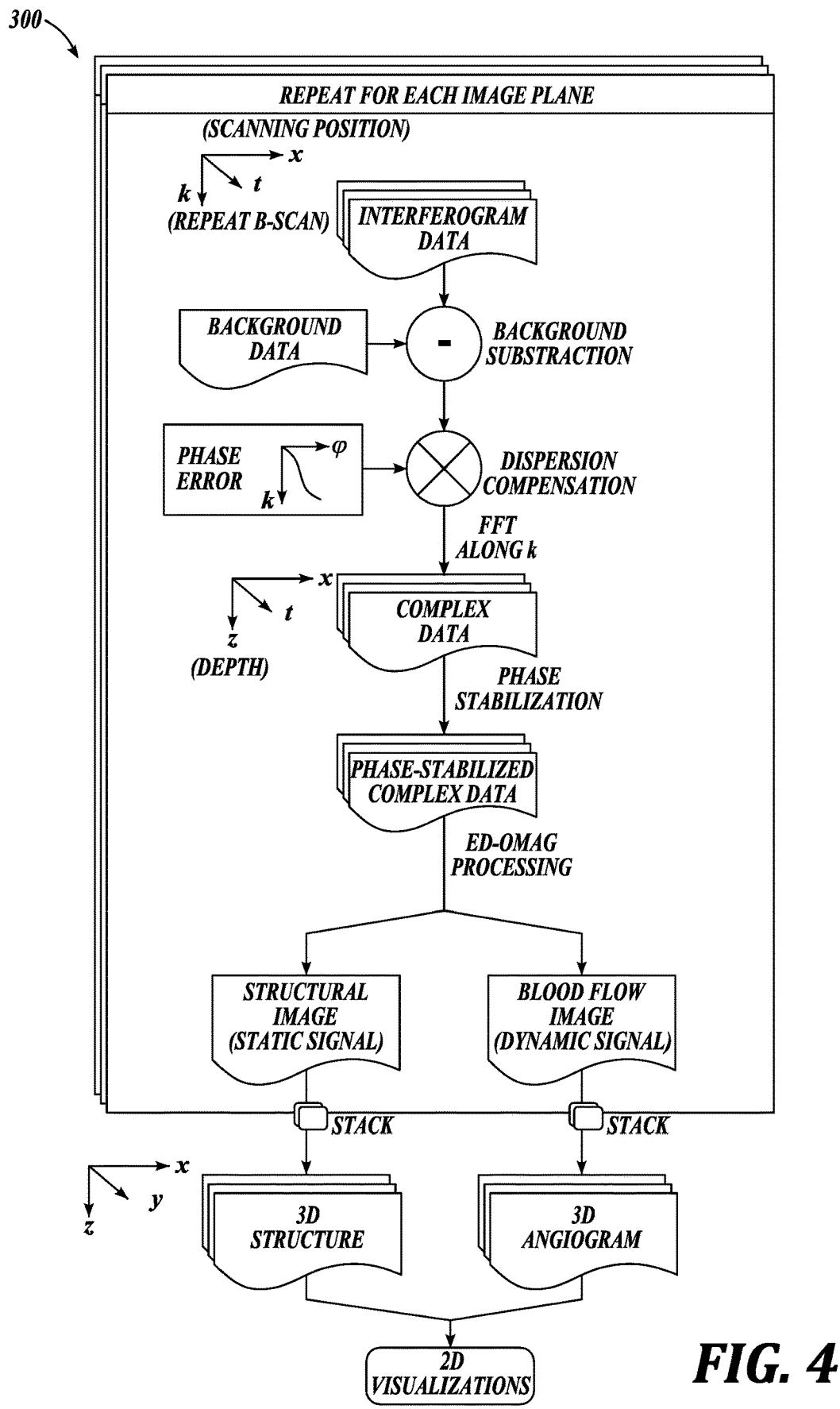
FIG. 4 is a flow chart of data processing procedure in accordance with an embodiment of the present technology.

FIG. 4 is a flow chart of data processing procedure in accordance with an embodiment of the present technology. In some embodiments, the procedures for imaging premature infants are briefly as follows: 1) Infant subject is laid with a comfortable position on their back (i.e., in a supine position), and vital signs of subject to be suitable for imaging are confirmed; 2) The hand-held probe is then approached to subject right eye (OD) by a clinical operator; 3) The subject's iris is positioned at the center of iris view image; 4) The on-probe joystick is used to adjust reference delay, so that the OCT image of retina is positioned in the middle of system ranging on the display; 5) The joystick is used to control reference polarization, and maximize OCT image intensity; and 6) When confirmed ready, start button on the joystick is pushed to start data acquisition. The probe is maintained still during imaging with assistance from iris viewer.

The procedures for imaging adult subjects follow similar protocol for imaging premature infants, except that no vital sign monitoring is necessary. Images may be taken with the subject and operator both at sitting position. Operators may rest their elbows on a desk and use two fingers as spacer between the probe and subject's eye lids. The subject is asked to stare at the fixation screen inside the probe. Generally, no external fixation or support device is required. All data collected are processed offline after imaging sessions.

Scanning Protocol

Depending on the scanning mode, the hand-held OCT has three categories of scanning protocol: 1) 2D preview mode: x axis galvo scans through one horizontal line on retina to form one B-scan, and then y-axis galvo scans through a vertical line, forming a set of orthogonal B-scan imaging planes. This pattern is repeated at video rate, until operator is satisfied with targeting. In some embodiments, A-line number per B-scan is 500. 2) 3D OCTA mode: 400 A-line per B-scan, 4 repeated B-scans per imaging plane, 400 planes, and total image number: 1600. Bi-directional B-scan protocol may be utilized in order to eliminate time required for galvo fly-back, thus optimizing imaging throughput. Image acquisition time may be only 3.2 seconds, with B-scan interval of 2.5 ms. 3) 3D structural OCT mode: similar scan protocol to OCTA, but without repeated scanned at each B-scan position. The resultant image volume contains 400 B-scan images, with 400 A-lines per B-scan. Imaging collection time is 0.8 second.

Data Processing and Visualization

As described by the scanning protocol section above, each volumetric C-scan is formed by a stack of B-scans. With OCTA imaging protocol, each group of repeated B-scans is processed into two images, one being the OCT structural image and another the OCTA angiogram. A procedure 300 for the data processing is summarized as follows: 1) Raw data from digitizer is re-assembled to a 2D array, with first dimension as wavelength, and second dimension is A-line index, i.e. lateral position. 2) Raw spectrum is convolved with a phase vector, to compensate for dispersion mismatch. This phase vector is obtained from a calibration procedure described herein. 3) FFT is performed along k, and half of the resultant 2D array is truncated, forming a complex B-scan image. 4) Each group of complex B-scan images is processed by a robust numerical phase-stabilization algorithm. 5) Eigen-decomposition-based OMAG algorithm is applied to separate blood flow signal from static signal, forming two images. 6) Repeating the above steps for all imaging planes assembles a C-scan. Each OCTA C-scan produces two volumes of 3D images, one for structure, and one for angiogram.

Imaging result visualizations are processed following OCTA conventions, where image segmentation is performed on entire volume to separate the vascular networks in different layers. In some embodiments, the retina may be segmented into three layers: the superficial retina from ganglion cell layer (GCL) to inner plexiform layer (IPL), the deep retina from inner nuclear layer (INL) to outer plexiform layer (OPL) and the outer retina from outer nuclear layer (ONL) to external limiting membrane (ELM). The choroid layer was segmented from retinal pigment epithelium (RPE) to 200 μm below the RPE. In addition, choriocapillaris, which was 20 μm-thick layer located 20 μm below the RPE, may also be segmented. Maximum intensity projection is provided for visualizing blood vessel networks in en-face view 52EF. In some embodiments, false color maps of retinal vasculature are produced by coding superficial retinal as red and deep retinal as green to better visualize the depth-resolved vasculatures. Field-of-view on retina is estimated from scanning angle and axial eye length.

Field-of-View Calibration

Figure 5B:
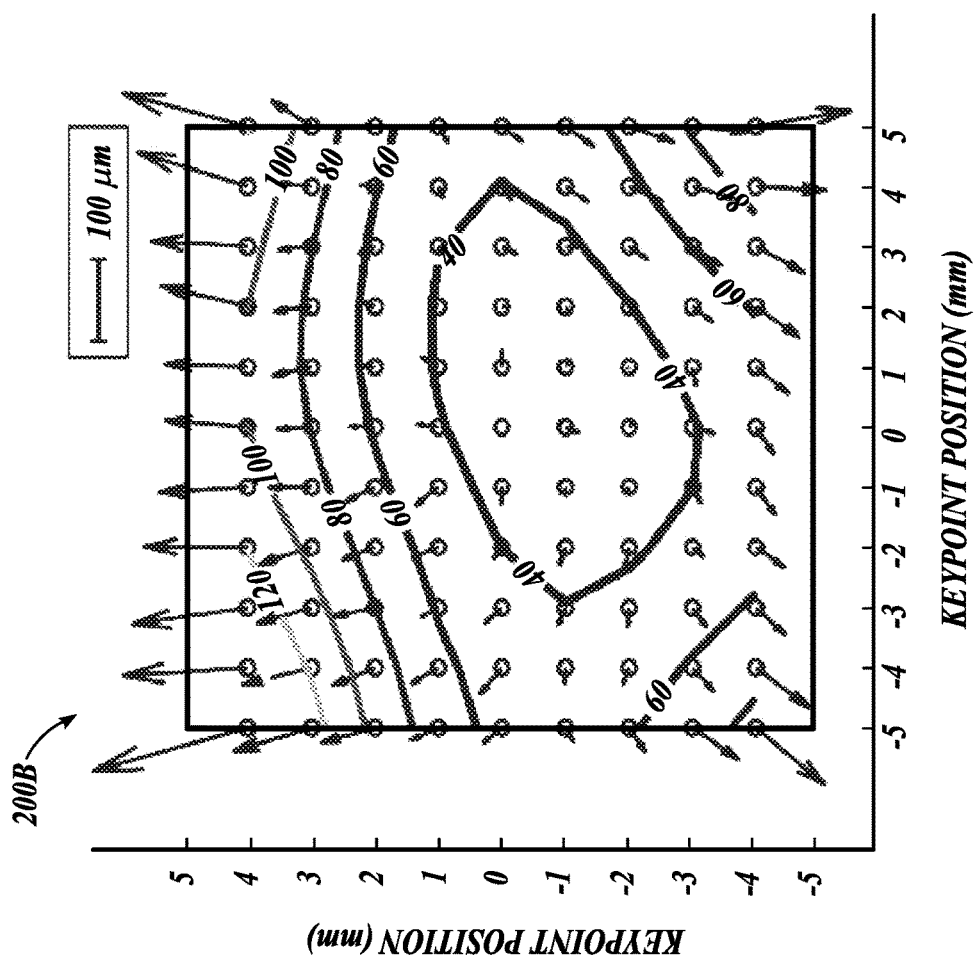
FIGS. 5A and 5B show field-of-view calibration results in accordance with an embodiment of the present technology.
Figure 5A:
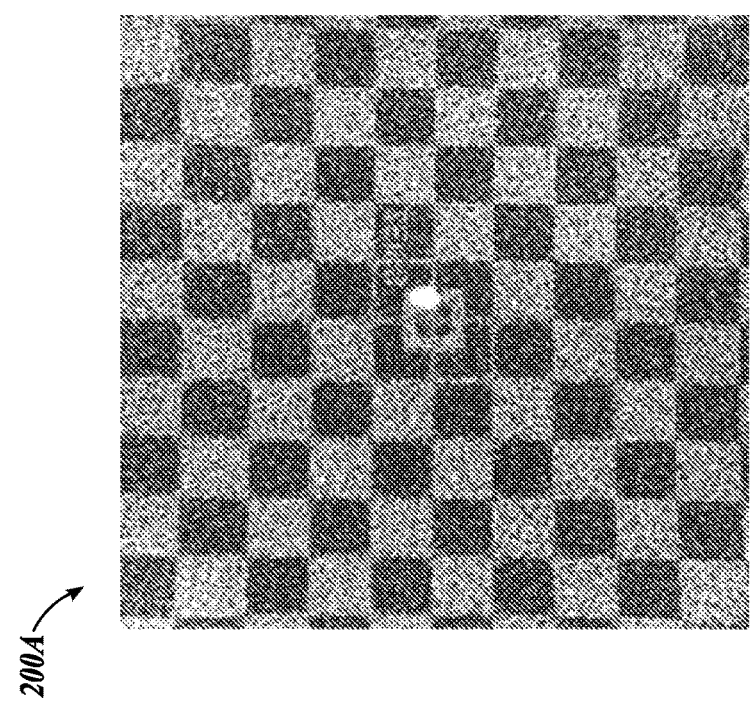

FIGS. 5A and 5B show field-of-view calibration results in accordance with an embodiment of the present technology. In some embodiments, to test the imaging field of view and to calibrate image distortion on the HH-OCTA system, a phantom model eye is used as a calibration target. A model eye may be specially designed to simulate adult human eyeball with a checker-board pattern 200A printed on retinal-mimicking surface. The pattern is used to calibrate commercial OCT systems. In sample embodiments, the total size of the checker-board pattern is 12×12 mm$^2$, and size of each box on the pattern is 1×1 mm$^2$. Center of the pattern may be aligned with fovea. The model eye may be mounted on a custom-built cage in order to precisely align to the hand-held probe. During calibration, a 3D volume with 400×400 A-lines may be acquired by the HH-OCT system with maximum field-of-view.

The en-face maximum intensity projection image is presented in FIG. 5A. Here, the field of view on adult retina is estimated to be slightly over 10 mm by 10 mm After applying checkerboard pattern key points detection algorithm, the image distortion field may be calculated by comparing to the standard pattern. The resultant distortion vector map 200B is shown in FIG. 5B, together with contour plot showing the distortion amplitude. Most area of the field-of-view has distortion less than 100 μm, and the mean amplitude of distortion is 57.1 μm. Top portion of the image presents larger distortion due to lower scanning velocity at the beginning of each B-scan. Nevertheless, the overall distortion of image meets the distortion requirement of the standard for visualization and quantification purposes. In some embodiments, when further improvement of image fidelity is required, an evenly spaced sampling grid can be derived from the distortion vector map, so that images can be re-sampled accordingly, to eliminate field distortion.

FIGS. 6A-6E show images displayed on the on-probe display 50 in accordance with an embodiment of the present technology. All scale bars are 1 mm. These sample images may be displayed on the operator screen (SCRo) 42 and the fixation screen (SCRf) 43 during the imaging procedure to guide the operator, as explained above. In the illustrated embodiment, retina imaging was conducted on a healthy adult volunteer, with OCTA scanning protocol. As the duration of the procedure is an essential metric for user experience, a stop-watch was used to record the time for completing each step of our imaging. The time required to target at macular region was below 10 seconds in 8 out of 10 attempts, and approximately 20 seconds were required to optimize the image by maneuvering the positioning of the probe and adjusting the system polarization.

OCT Structural Images

Typical OCT intensity image results from a normal subject (e.g., OD, 29 year male) are presented in the form of en-face average intensity projection 52RE in FIG. 6D. The wide-field imaging had a scan area of 10×10 mm$^2$. In the wide-field structural projection image of FIG. 6D an overview of the retina is visualized. Large and medium sized blood vessel are also visible.

Two selected B-scans 52B of FIGS. 6A and 6B are presented at cross-sectional planes on fovea and optic nerve head. In these images, each physiological layer in the retina can be individually identified. The imaging system also provides sufficient sensitivity to show sparsely distributed hyper-reflective opacities in vitreous, as well as to visualize the posterior cortical vitreous.

To further guide the operator, the operator screen 42 also includes an iris image 52IR shown in FIG. 6C. FIG. 6E shows a sample fixation image 52PE that is visible to a patient.

Figure 7A:
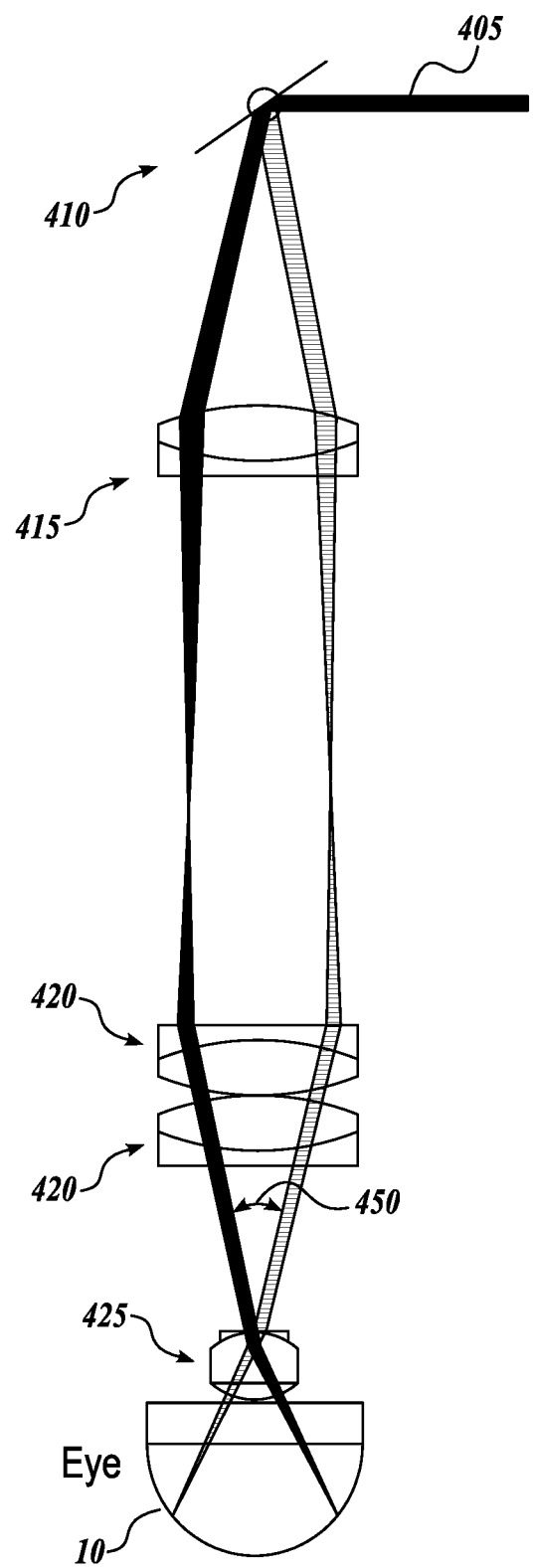
FIG. 7A shows a simplified optical configuration schematic using scan lens to realize OCT/OCTA imaging in accordance with an embodiment of the present technology.

FIG. 7A shows a simplified optical configuration schematic using scan lens to realize OCT/OCTA imaging in accordance with an embodiment of the present technology. In operation, an incoming beam 405 is reflected off a scan mirror 410 toward a scan lens 415. The expanded beam 405 proceeds to an ophthalmic lens 420. The beam 405 passes through iris 425 to illuminate eye 10. However, the above-described setup may result in a beam that is relatively narrow field-of-view of about 40 degrees viewing angle (at pupil entrance). Although this field-of-view angle 450 may be considered as a wide-field OCT/OCTA in the conventional technology, such angle may be insufficient to cover peripheral retina, where the characteristics of RoP are important. Therefore, in some embodiments, the beam may be expanded using the curved mirror, as described with reference to FIGS. 7B and 7C below.

Figure 7C:
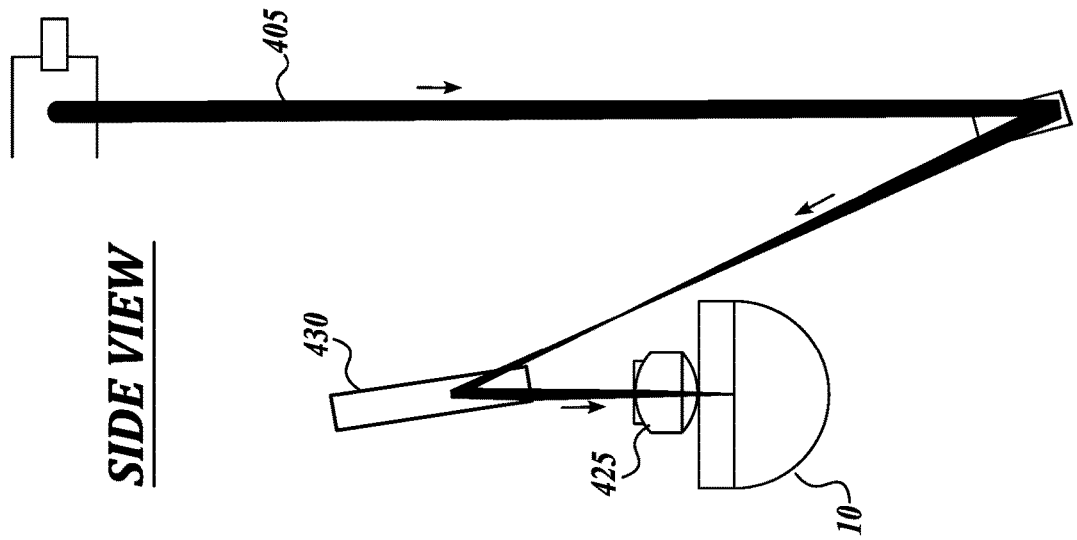
FIGS. 7B and 7C show a schematic of scan optics that uses curved mirrors in accordance with an embodiment of the present technology.
Figure 7B:
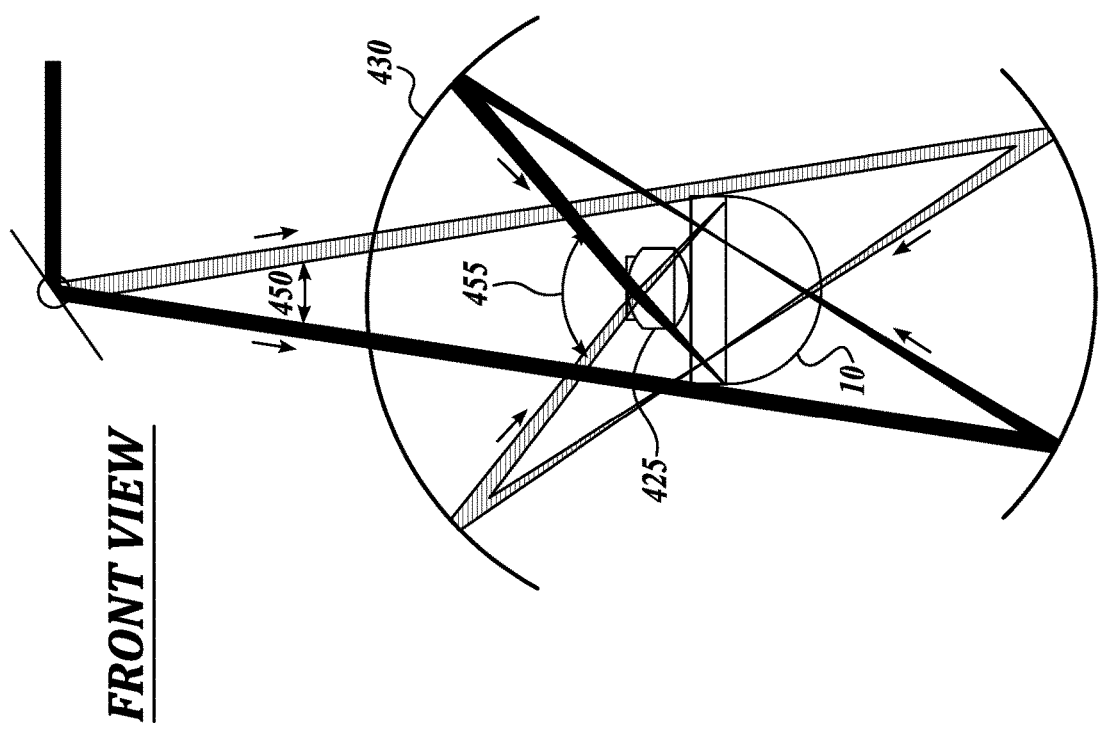

FIGS. 7B and 7C show a schematic of scan optics that uses curved mirrors in accordance with an embodiment of the present technology. The illustrated embodiments rely on multiple curved mirrors 430 to realize ultra-wide scanning angle 455 (at pupil nodal plane). Using this configuration, a maximum scanning angle of over 90 degrees can be achieved.

Figure 8:
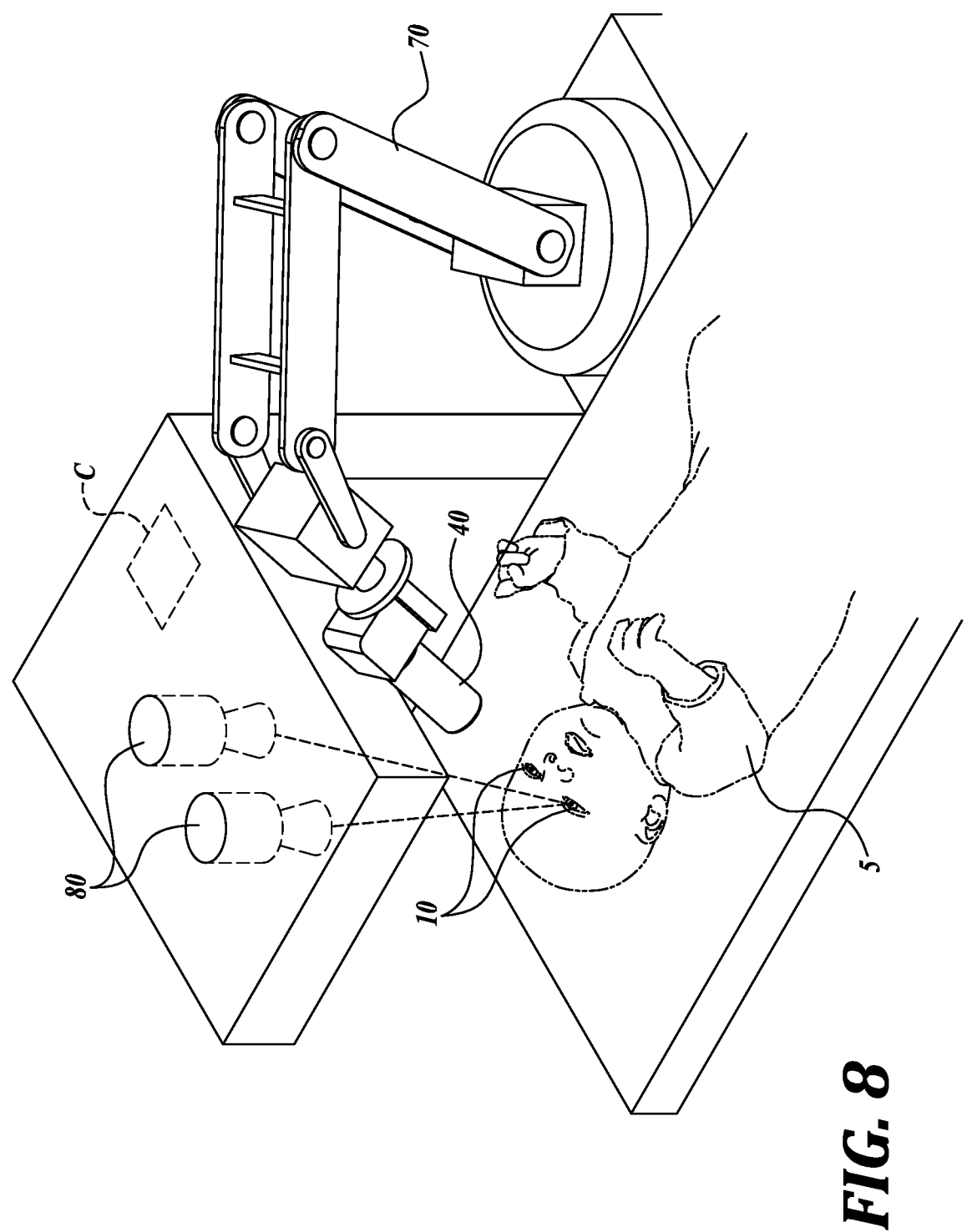
FIG. 8 shows a robotic motion-tracking mechanism for OCT/OCTA imaging in accordance with an embodiment of the present technology.

FIG. 8 shows a robotic motion-tracking mechanism for OCT/OCTA imaging in accordance with an embodiment of the present technology. In some embodiments, motion artifacts are a major barrier for obtaining reliable images. In many embodiments, using two fingers as a spacer between the hand-held OCT probe and the subject's eye, the operator becomes significantly more confident to stabilize the probe during imaging. However, motions from the subject, especially from uncooperative infants, can also deteriorate the image quality, especially with the more demanding OCTA images. In general, higher speed swept lasers, advanced scanning protocols and post-processing stabilization techniques help to reduce the scanning time and achieve higher OCTA image fidelity. In some embodiments, the hand-held probe 40 may be integrated with active tracking mechanisms, such as a robotic arm 70, to track the movement of infant's head and eye motions. A side-mounted 3D imaging sensor (e.g. a set of stereo camera) 80 can be employed to capture the head motion. Images captured by the on-board iris viewer camera (shown in FIG. 3B) can be used as the reference of eye rotation. Instructions of counter-movements may be calculated by a controller C based on the reference images and sent to tracking mechanism.

In some embodiments, the operator may use an augmented reality (AR). For example, the operator may wear a head-mounted display (e.g. AR glasses or goggles, not shown) in which a miniaturized display screen 42 can be used to display monitoring and real-time OCT images, meanwhile allowing the operator to see the test subject (infant) upon which to guide the operator to conduct the imaging.

FIGS. 9A-9D show OCT sample imaging results acquired from pre-mature infants by a hand-held unit in accordance with an embodiment of the present technology. In particular, FIGS. 9A and 9C show en-face average intensity projection, and FIGS. 9B and 9D each shows three selected cross-section B-scans from 3-D scan result. The imaging planes are indicated by dashed lines 1, 2, 3 in en-face projection image. Results were obtained from an infant of 28-week gestational age, with an imaging field of view at 3.6 mm×3.6 mm: All scale bars correspond to 1 mm length.

Preliminary imaging sessions were performed on seven premature infants in NICU. The infants had a mean (±SD) gestational age of 198 (±23) days. Mean (SD) postmenstrual age (PMA) at imaging was 256 (±23) days. There were two operators involved in this study with extensive experiences using a commercially available hand-held ophthalmology OCT system (Envisu C2300, Leica Microsystems). Both operators reported that the prototype hand-held OCT system used in this study was significantly more comfortable and efficient, due to the introduction of iris viewer and on-probe display that provides rich visual feedback when positioning the probe. This was also confirmed by statistics of time consumption during imaging sessions. The imaging system was able to capture a first retina image for 85% (6/7) subjects in under 30 seconds. Compared to a previous study where only 31% of imaging sessions were able to capture an image in <1 minute, indicating that the prototype hand-held OCT system reported here is over four times more time efficient. Due to the difference in eye axial length between infants and adults, the FoV is effectively smaller on infants. For example, for the same scanning angle, 10 mm scanning range on adult retina is equivalent to 6.3 mm on a 32-week PMA infant.

Figure 10A:
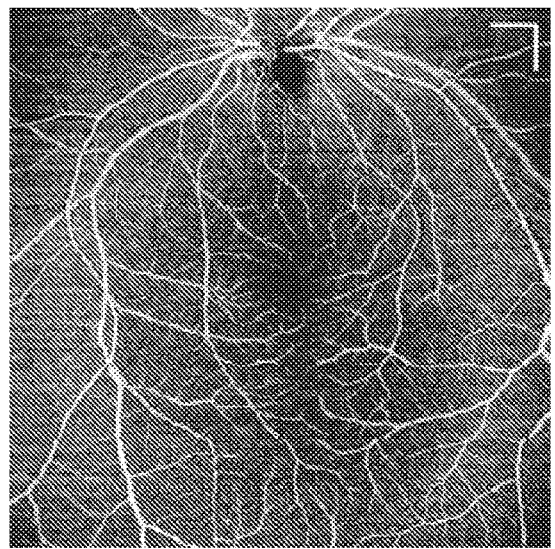
FIGS. 10A-10G show sample OCTA imaging results acquired from healthy adults by a hand-held unit in accordance with an embodiment of the present technology.
Figure 10B:
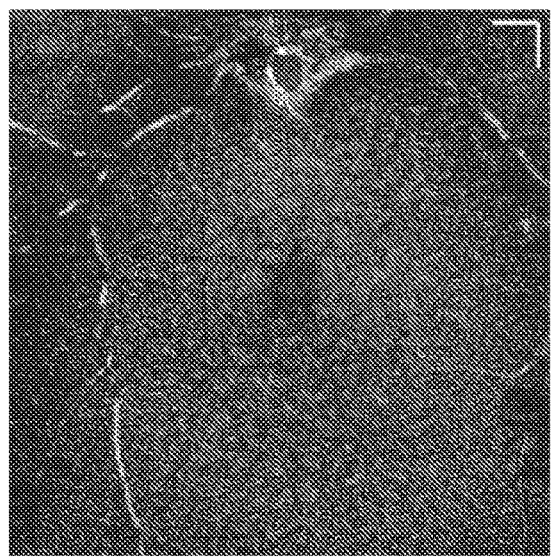
Figure 10C:
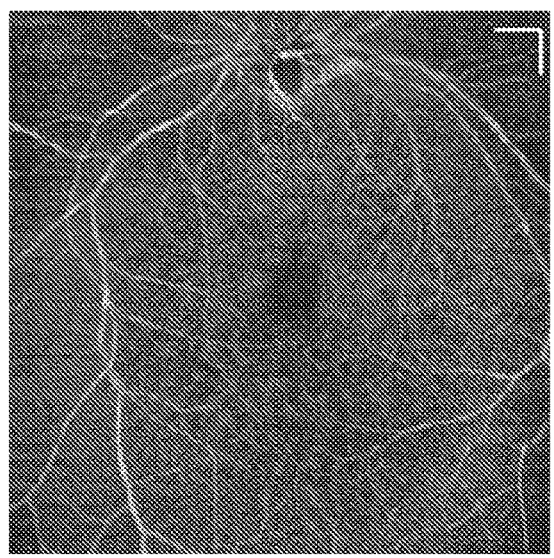
Figure 10D:
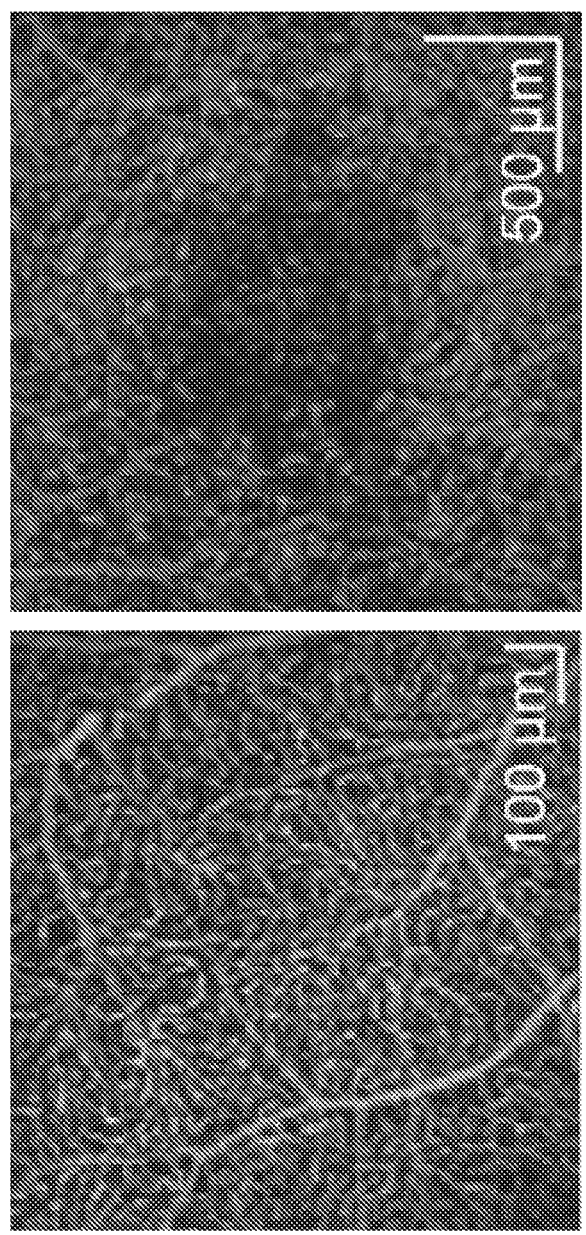
Figure 10G:
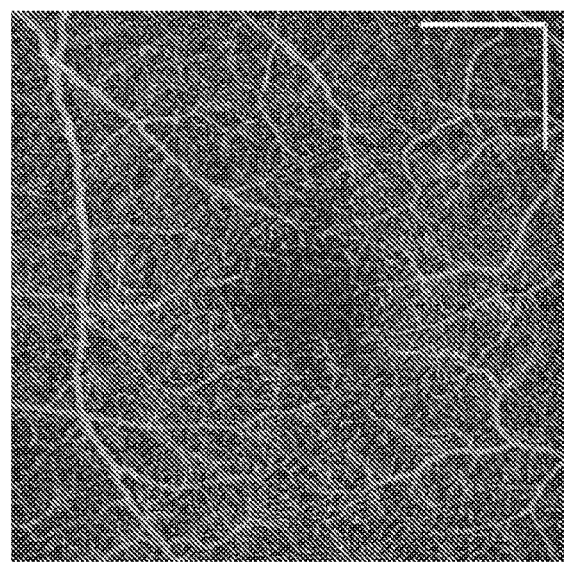
Figure 10F:
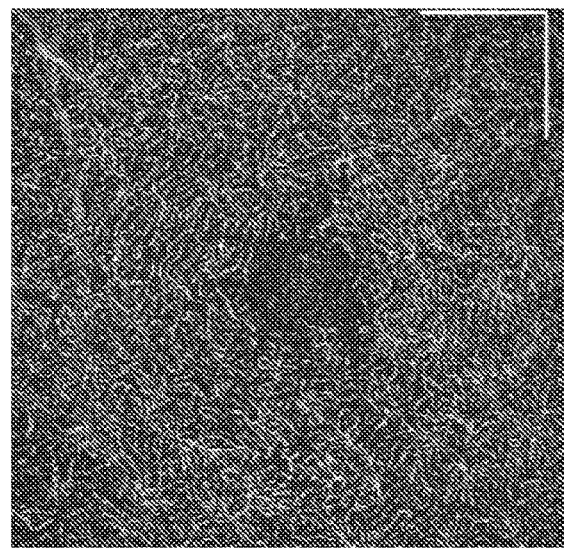
Figure 10E:
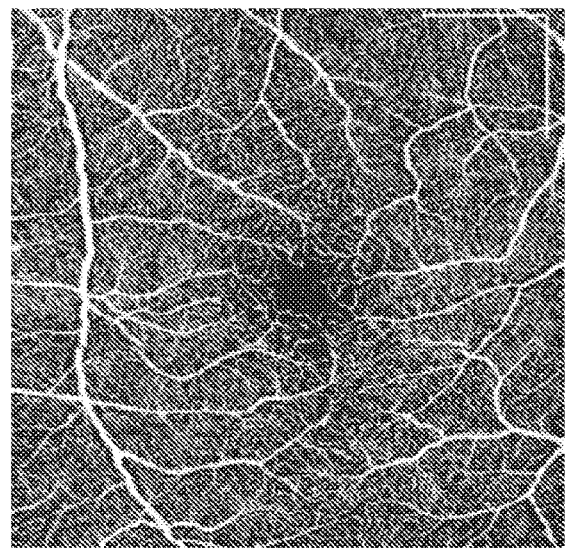

FIGS. 10A-10G show OCTA imaging results acquired from a healthy adult by a hand-held unit in accordance with an embodiment of the present technology Imaging results has shown that a hand-held OCTA system used in this study is capable of providing capillary-level resolution en face OCTA images. Superficial and deep retina angiography with wide field-of-view are shown in FIGS. 10A and 10B, respectively. Images were produced by maximum intensity projection (MIP) of corresponding layers. False color image is presented in FIG. 10C, where superficial and deep retina layers are color coded, so the retinal vessel morphology, as well as depth information can be presented in the same image. FIG. 10D shows two partially enlarged images from FIG. 10C, one from lower left region (1×1 mm$^2$), and one from central fovea (2.5×2.5 mm$^2$), so that the details of angiogram are depicted. The capillary vessels can still be resolved, even at this large field-of-view. Higher magnification retinal images were collected using smaller FoV and results are displayed in FIGS. 10E-10G: en face MIP images of superficial retina layer in FIG. 10E, deep retina layer in FIG. 10F, and false-color depth encoded image in FIG. 10G. The parafoveal capillaries are clearly visible, thereby allowing visualization of the foveal avascular zone (FAZ). Vascular ring is visible around the FAZ, and capillary vascular density appears to increase radially with the increase of its distance to the foveal center, which can be observed on both superficial retina (FIG. 10E) and deep retina (FIG. 10F) layers. For choroid layers, due to the limitations in system lateral resolution, the detailed structure of choriocapillaris is not visible, so the projection images are omitted here.

Many embodiments of the technology described above may take the form of computer- or controller-executable instructions, including routines executed by a programmable computer or controller. Those skilled in the relevant art will appreciate that the technology can be practiced on computer/controller systems other than those shown and described above. The technology can be embodied in a special-purpose computer, controller or data processor that is specifically programmed, configured or constructed to perform one or more of the computer-executable instructions described above. Accordingly, the terms "computer" and "controller" as generally used herein refer to any data processor and can include Internet appliances and hand-held devices (including palm-top computers, wearable computers, cellular or mobile phones, multi-processor systems, processor-based or programmable consumer electronics, network computers, mini computers and the like).

From the foregoing, it will be appreciated that specific embodiments of the technology have been described herein for purposes of illustration, but that various modifications may be made without deviating from the disclosure. Moreover, while various advantages and features associated with certain embodiments have been described above in the context of those embodiments, other embodiments may also exhibit such advantages and/or features, and not all embodiments need necessarily exhibit such advantages and/or features to fall within the scope of the technology. Accordingly, the disclosure can encompass other embodiments not expressly shown or described herein.

What is claimed is:

1. An optical coherence tomography (OCT) system, comprising an OCT probe that is configured as a hand-held probe for imaging an eye of a patient, the OCT probe comprising:
    an OCT optical system configured to direct a source OCT signal to the eye and configured to capture OCT scan signal returning from the eye; and
    an on-probe display carried by a handle, wherein the on-probe display is configured to display imaging data of the eye of a patient to an operator during OCT imaging,
    wherein the imaging data of the eye that is displayed on the on-probe display comprise two B-scan images, wherein the on-probe display is configured to display an en-face image within an en-face image display area of the on-probe display, and wherein the en-face image is an image of an average intensity projection of the eye of the patient.

2. The OCT system of claim 1, wherein the two B-scan images are obtained at two mutually orthogonal planes.

3. The OCT system of claim 1, further comprising an iris viewer integrated into the OCT probe, wherein the iris viewer is configured to assist the operator to target the patient's eye during imaging, and wherein the iris viewer includes:
 a source of illumination configured to be directed towards an iris of the patient's eye; and
 a detector configured to receive light reflected from the patient's eye,
 wherein the on-probe display is configured to display an iris image within an iris display area of the on-probe display.

4. The OCT system of claim 1, wherein the en-face image is an image of an average intensity projection of the eye of the patient.

5. The OCT system of claim 1, wherein the on-probe display is configured to display a fixation image within a fixation image display area of the on-probe display.

6. The OCT system of claim 1, wherein the on-probe display is a monolithic display comprising zones for different images.

7. The OCT system of claim 1, further comprising a computer configured to process the OCT data to provide the OCT imaging data, wherein the computer is physically separate from, but in electronic communication with the OCT probe.

8. The OCT system of claim 1, further comprising an operating switch attached to the OCT probe, wherein the operating switch is configured to control image acquisition of the OCT system.

9. The OCT system of claim 1, wherein the OCT probe comprises an electrically tunable lens configured to automatically control a focus of the source OCT signal focus during OCT imaging.

10. The OCT system of claim 1, wherein the OCT probe comprises curved mirrors configured to obtain wide field-of-view images.

11. An optical coherence tomography (OCT) system, comprising an OCT probe that is configured as a hand-held probe for imaging an eye of a patient, the OCT probe comprising:
 an OCT optical system configured to direct a source OCT signal to the eye and configured to capture OCT scan signal returning from the eye;
 an on-probe display carried by a handle, wherein the on-probe display is configured to display imaging data of the eye of a patient to an operator during OCT imaging;
 a robotic motion-tracking mechanism configured to stabilize OCT imaging; and
 a 3D imaging sensor configured to capture head motion of the patient.

12. A method of generating an optical coherence tomography (OCT) image of an eye of a patient, comprising:
 directing an OCT probing beam to the eye by a hand-held OCT probe of an OCT system;
 capturing OCT scan signal returning from the eye;
 generating OCT and OCTA images from the OCT scan signal by a computer configured to process the OCT signal, wherein the computer is physically separate from, but in electronic communication with the OCT probe;
 displaying OCT images on an on-probe display carried by a handle of the OCT; and
 guiding the hand-held OCT probe by the OCT images displayed on the on-probe display,
 wherein the OCT images on the on-probe display comprise at least two orthogonal B-scan images, and wherein the hand-held probe further comprises an iris viewer integrated into the OCT probe,
 the method further comprising:
 capturing an iris image of the eye of the patient;
 displaying the iris image within an iris display area of the on-probe display; and
 displaying an en-face image within an en-face image display area of the on-probe display, wherein the en-face image is an image of a retina of the patient or an average intensity projection of the eye of the patient.

13. The method of claim 12, further comprising:
 displaying a fixation image within a fixation image display area of the on-probe display.

14. The method of claim 12, wherein the patient is an infant.

15. A method of generating an optical coherence tomography (OCT) image of an eye of a patient, comprising:
 directing an OCT probing beam to the eye by a hand-held OCT probe of an OCT system;
 capturing OCT scan signal returning from the eye;
 generating OCT and OCTA images from the OCT scan signal by a computer configured to process the OCT signal, wherein the computer is physically separate from, but in electronic communication with the OCT probe;
 displaying OCT images on an on-probe display carried by a handle of the OCT;
 guiding the hand-held OCT probe by the OCT images displayed on the on-probe display;
 capturing head motion of the patient by a 3D imaging sensor; and
 based on the head motion, stabilizing the OCT probe by a robotic motion-tracking mechanism that carries the OCT probe.

\* \* \* \* \*

UNITED STATES PATENT AND TRADEMARK OFFICE
CERTIFICATE OF CORRECTION

PATENT NO. : 12,239,376 B2  
APPLICATION NO. : 17/593999  
DATED : March 4, 2025  
INVENTOR(S) : Ruikang K. Wang et al.

Page 1 of 1

It is certified that error appears in the above-identified patent and that said Letters Patent is hereby corrected as shown below:

On the Title Page

| Column | Line | |
|---|---|---|
| 1 | 1 | item (73), in "Assignee", delete "The University" and insert -- University -- |

Signed and Sealed this  
Tenth Day of February, 2026

John A. Squires  
*Director of the United States Patent and Trademark Office*